(12) United States Patent
Zhao et al.

(10) Patent No.: US 10,888,248 B2
(45) Date of Patent: Jan. 12, 2021

(54) DETERMINING POSITION OF MEDICAL DEVICE IN BRANCHED ANATOMICAL STRUCTURE

(71) Applicant: Intuitive Surgical Operations, Inc., Sunnyvale, CA (US)

(72) Inventors: Tao Zhao, Sunnyvale, CA (US); Giuseppe Maria Prisco, Calci (IT)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 893 days.

(21) Appl. No.: 15/486,246

(22) Filed: Apr. 12, 2017

(65) Prior Publication Data

US 2017/0311844 A1 Nov. 2, 2017

Related U.S. Application Data

(63) Continuation of application No. 14/048,331, filed on Oct. 8, 2013, now abandoned.
(Continued)

(51) Int. Cl.
*A61B 5/00* (2006.01)
*A61B 5/06* (2006.01)
(Continued)

(52) U.S. Cl.
CPC ............ *A61B 5/066* (2013.01); *A61B 1/0005* (2013.01); *A61B 1/2676* (2013.01);
(Continued)

(58) Field of Classification Search
CPC ....... A61B 5/066; A61B 34/20; A61B 5/0059; A61B 5/064; A61B 1/2676; A61B 1/0005;
(Continued)

(56) References Cited

U.S. PATENT DOCUMENTS 5,680,481 A 10/1997 Prasad
6,351,573 B1 2/2002 Schneider
(Continued)

FOREIGN PATENT DOCUMENTS

CN 102439631 A 5/2012
EP 2884879 A1 6/2015
(Continued)

OTHER PUBLICATIONS

Extended European Search Report for Application No. 13845361.8, dated May 20, 2016, 10 pages.
(Continued)

*Primary Examiner* — Joel Lamprecht
(74) *Attorney, Agent, or Firm* — Fish & Richardson P.C.

(57) ABSTRACT

Information extracted from sequential images captured from the perspective of a distal end of a medical device moving through an anatomical structure are compared with corresponding information extracted from a computer model of the anatomical structure. A most likely match between the information extracted from the sequential images and the corresponding information extracted from the computer model is then determined using probabilities associated with a set of potential matches so as to register the computer model of the anatomical structure to the medical device and thereby determine the lumen of the anatomical structure which the medical device is currently in. Sensor information may be used to limit the set of potential matches. Feature attributes associated with the sequence of images and the set of potential matches may be quantitatively compared as part of the determination of the most likely match.

20 Claims, 10 Drawing Sheets

Related U.S. Application Data

(60) Provisional application No. 61/713,010, filed on Oct. 12, 2012.

(51) Int. Cl.
| | | |
|---|---|---|
| *G06T 7/73* | (2017.01) | |
| *A61B 1/00* | (2006.01) | |
| *A61B 1/267* | (2006.01) | |
| *A61B 34/20* | (2016.01) | |
| A61B 6/12 | (2006.01) | |
| A61B 6/00 | (2006.01) | |
| A61B 8/08 | (2006.01) | |
| A61B 34/10 | (2016.01) | |
| A61B 90/00 | (2016.01) | |

(52) U.S. Cl.
CPC ............ *A61B 5/0059* (2013.01); *A61B 5/064* (2013.01); *A61B 34/20* (2016.02); *G06T 7/75* (2017.01); *A61B 6/12* (2013.01); *A61B 6/5247* (2013.01); *A61B 8/0841* (2013.01); *A61B 8/5261* (2013.01); *A61B 2034/105* (2016.02); *A61B 2034/2065* (2016.02); *A61B 2090/365* (2016.02); *G06T 2207/10016* (2013.01); *G06T 2207/10068* (2013.01); *G06T 2207/30004* (2013.01)

(58) Field of Classification Search
CPC ...... A61B 2034/2065; A61B 2090/365; A61B 2034/105; A61B 8/5261; A61B 8/0841; A61B 6/5247; A61B 6/12; A61B 17/00234; A61B 1/05; G06T 7/75; G06T 2207/30004; G06T 2207/10068; G06T 2207/10016; A61M 2025/09166; A61M 25/00
See application file for complete search history.

(56) References Cited

U.S. PATENT DOCUMENTS

| | | |
|---|---|---|
| 7,756,563 B2 | 7/2010 | Higgins |
| 2001/0031920 A1 | 10/2001 | Kaufman |
| 2005/0107679 A1 | 5/2005 | Geiger et al. |
| 2005/0182295 A1 | 8/2005 | Soper et al. |
| 2005/0182319 A1 | 8/2005 | Glossop |
| 2005/0261550 A1 | 11/2005 | Akimoto |
| 2007/0156019 A1 | 7/2007 | Larkin |
| 2008/0207997 A1 | 8/2008 | Higgins et al. |
| 2008/0212082 A1 | 9/2008 | Froggat |
| 2008/0218770 A1 | 9/2008 | Moll |
| 2009/0054729 A1 | 2/2009 | Mori et al. |
| 2009/0324161 A1 | 12/2009 | Prisco |
| 2010/0249506 A1 | 9/2010 | Prisco |
| 2012/0004537 A1 | 1/2012 | Tolkowsky et al. |
| 2012/0059220 A1 | 3/2012 | Holsing et al. |
| 2012/0062714 A1 | 3/2012 | Liu et al. |
| 2012/0203067 A1* | 8/2012 | Higgins ............ A61B 1/00006 600/117 |
| 2012/0289777 A1 | 11/2012 | Chopra |
| 2014/0180063 A1 | 6/2014 | Zhao et al. |
| 2018/0220883 A1* | 8/2018 | Higgins ............ A61B 1/00009 |

FOREIGN PATENT DOCUMENTS

| | | |
|---|---|---|
| JP | 2013517909 A | 5/2013 |
| WO | WO-2008125910 A2 | 10/2008 |
| WO | WO-2009097461 A1 | 8/2009 |
| WO | WO-2010128411 A1 | 11/2010 |
| WO | WO-2011094518 A2 | 8/2011 |
| WO | WO-2014028394 A1 | 2/2014 |

OTHER PUBLICATIONS

Hartley R., et al., "3D Reconstruction of Cameras and structure", in: Multiple View Geometry in Computer Vision, Cambridge University Press, Chapter 10, 2nd Edition, 2004, pp. 262-278.

Helferty J.P., et al., "Computer-based System for the Virtual-Endoscopic Guidance of Bronchoscopy," Computer Vision and Image Understanding, US, Sep. 1, 2007, vol. 108, No. 1-2, pp. 171-187, XP022227950, ISSN: 1077-3142.

International Search Report and Written Opinion for Application No. PCT/US13/63813, dated Jan. 8, 2014, 12 pages.

Luo X., et al., "On Scale Invariant Features and Sequential Monte Carlo Sampling for Bronchoscope Tracking," Medical Imaging 2011: Visualization, Image-Guided Procedures, and Modeling, edited by Wong K.H., et al., Proceedings of SPIE, vol. 7964, 796400.

Office Action dated Sep. 26, 2016 for Chinese Application No. 201380053469.5 filed Oct. 8, 2013, 15 pages.

Soper T.D., et al., "In Vivo Validation of a Hybrid Tracking System for Navigation of an Ultrathin Bronchoscope within Peripheral Airways," IEEE Transactions on Biomedical Engineering, 2010, vol. 57 (3), pp. 736-745.

Tomasic., et al., "Factoring Image Sequences into Shape and Motion," Proceedings of the IEEE Workshop on Visual Motion, 1991, pp. 21-28.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

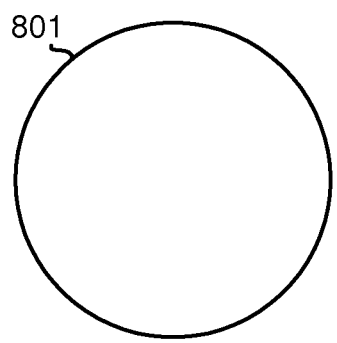
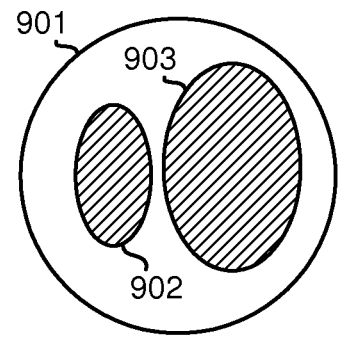
fig.8
fig.9
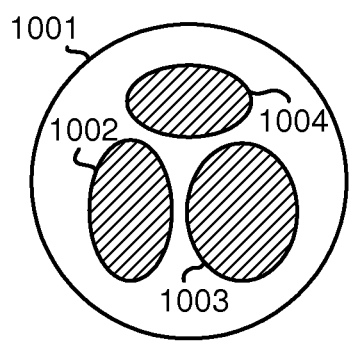
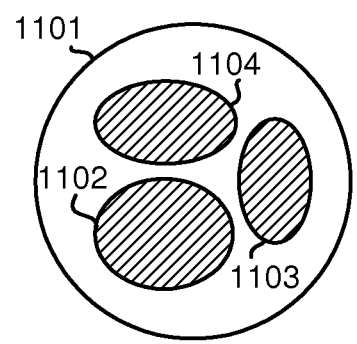
fig.10
fig.11
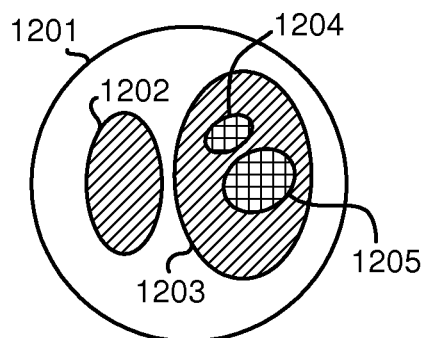
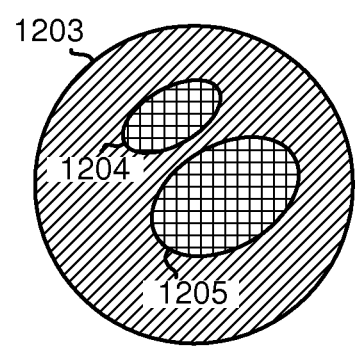
fig.12
fig.13

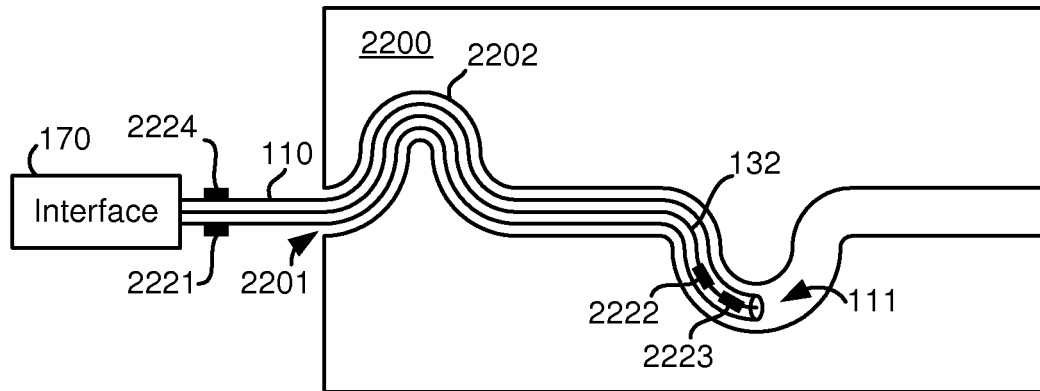
fig.22
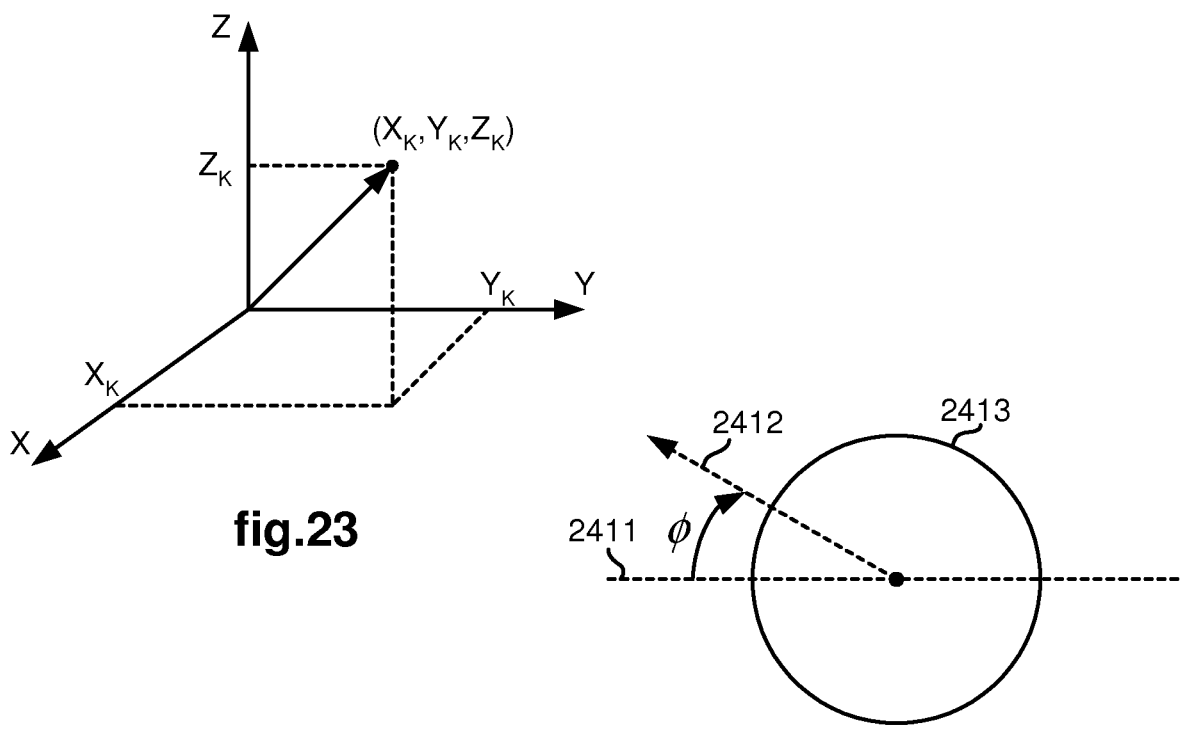
fig.23
fig.24

DETERMINING POSITION OF MEDICAL DEVICE IN BRANCHED ANATOMICAL STRUCTURE

CROSS-REFERENCE TO RELATED APPLICATIONS

This is a continuation of U.S. application Ser. No. 14/048,331, filed on Oct. 8, 2013, which claims priority to U.S. Provisional Application No. 61/713,010, filed on Oct. 12, 2012. The content of the prior applications are incorporated herein by reference into the disclosure of this application.

FIELD OF THE INVENTION

The present invention generally relates to medical systems and in particular, to a system and method for determining the position of a medical device in a branched anatomical structure by comparing information of images captured at a distal end of the medical device as it moves through the branched anatomical structure with corresponding information extracted from a computer model of the branched anatomical structure.

BACKGROUND

Image guided surgery helps surgeons navigate medical devices to targets in patients so that therapeutic and/or diagnostic medical procedures may be performed on the targets. For guidance, the position of a distal end of a medical device may be tracked and its image displayed along with or superimposed on a computer model of an anatomical structure associated with the target. The computer model may be generated from pre-operative and/or intra-operative patient anatomy scan data such as x-ray, ultrasound, fluoroscopy, computed tomography (CT), magnetic resonance imaging (MRI), and other imaging technologies. The medical device may be an endoscope, catheter, or medical instrument that has a steerable tip and flexible body capable of conforming to body passages or lumens leading to the target in a branched anatomical structure of the patient.

Proper registration of the medical device, anatomical structure, and computer model of the anatomical structure with respect to each other is desirable for accurate image guided surgery. Therefore, registration of these items is typically performed prior to performing a medical procedure on a patient. However, registration errors may develop during the performance of the medical procedure due to movement of the anatomical structure and/or difficulties in tracking the medical device as it moves through the anatomical structure. For continuously moving branched anatomical structures in which flexible medical devices are navigated to target areas, maintaining proper registration between tracked positions of medical devices and the branched anatomical structures is especially challenging.

U.S. 2005/0182319 describes tracking movement of anatomical structures using dynamic referencing and/or gating techniques and tracking movement of medical devices as they move inside anatomic structures using Electromagnetic (EM) tracking devices. However, due to inaccuracies at least partly attributed to the dynamic referencing, EM tracking devices and anatomical motion, accurate registration of medical devices moving through branched anatomical structures such as the lungs or heart are prone to error when a plurality of lumens in the branched anatomical structure reside within uncertainty regions resulting from such inaccuracies.

Luo, Xiongbiao et al. "On Scale Invariant Features and Sequential Monte Carlo Sampling for Bronchoscope Tracking," Medical Imaging 2011: Visualization, Image-Guided Procedures, and Modeling, edited by Kenneth H. Wong, David R. Homes III, Proc. Of SPIE Vol. 7964, 79640Q, describes a two-stage image-based method for determining a maximum similarity between a current bronchoscope camera frame and a generated virtual frame to determine a bronchoscope pose. The first stage predicts the inter-frame motion parameters between consecutive images of a bronchoscope video using scale invariant feature transform (SIFT) features and epipolar geometry analysis. The second stage recursively approximates the posterior probability density of the current bronchoscope camera pose in accordance with the estimated result of the first stage. Since the second stage generates a set of random samples that are defined as the camera motion parameters and the similarity between virtual bronchoscopic and patient specific real bronchoscopic images, the current camera motion parameters can be determined to be equal to the pose of one sample that corresponds to the maximum similarity inside the sample set. Although the method has been shown to provide good accuracy, the complexity of its calculations using Sequential Monte Carlo (SMC) methods is unsuitable for real-time applications with a computational time around 3.0 seconds per frame.

Soper, Timothy D. et al. "In Vivo Validation of a Hybrid Tracking System for Navigation of an Ultrathin Bronchoscope within Peripheral Airways," IEEE Transactions on Biomedical Engineering, Vol. 57, No. 3, March 2010, pp. 736-745, describes a hybrid approach in which both electromagnetic tracking (EMT) and image-based tracking (IBT) are employed along with an error state Kalman filter which adaptively estimates the localization error between the two tracking inputs. When the error becomes large, however, the system is incapable of self-correcting itself. Therefore, operator intervention may become necessary once the tracking diverges from the true path of the bronchoscope in an anatomical structure.

U.S. Pat. No. 7,756,563 describes a method to perform camera pose estimation in bronchoscopy by continuously aligning a live camera view to a corresponding view which has been rendered from a computer model. It assumes that the estimation from a previous frame is accurate to seed the iterative optimization of the current frame. The method, however, is not able to recover from any tracking failure which is very likely to occur in real life.

OBJECTS AND SUMMARY

Accordingly, one object of one or more aspects of the present invention is a medical system and method implemented therein for determining a position of a medical device in a branched anatomical structure as the medical device moves through the branched anatomical structure.

Another object of one or more aspects of the present invention is a medical system and method implemented therein that are self-correcting for determining a position of a medical device in a branched anatomical structure as the medical device moves through the branched anatomical structure.

Another object of one or more aspects of the present invention is a medical system and method implemented therein that are computationally efficient and suitable for real-time applications for determining a position of a medical device in a branched anatomical structure as the medical device moves through the branched anatomical structure.

Another object of one or more aspects of the present invention is a medical system and method implemented therein that provide accurate results for determining a position of a medical device in a branched anatomical structure as the medical device moves through the branched anatomical structure.

These and additional objects are accomplished by the various aspects of the present invention, wherein briefly stated, one aspect is medical system comprising: a memory storing information of a computer model of a branched anatomical structure; and a processor programmed to register the computer model to a medical device for determining a position of the medical device in the branched anatomical structure by determining a most likely match between information which has been extracted from a sequence of images that has been captured by an image capturing device from a perspective of a distal end of the medical device as the medical device moves through a plurality of lumens in the branched anatomical structure and corresponding information extracted from the computer model of the branched anatomical structure.

Another aspect is method for determining a position of the medical device in the branched anatomical structure, the method comprising: determining a most likely match between information extracted from a sequence of images that have been captured from a perspective of a distal end of a medical device as the medical device moves through a plurality of lumens in the branched anatomical structure and corresponding information extracted from the computer model of the branched anatomical structure.

Additional objects, features and advantages of the various aspects of the present invention will become apparent from the following description which should be taken in conjunction with the accompanying drawings.

BRIEF DESCRIPTION OF THE DRAWINGS

FIGS. 8-13 illustrate various examples of blob topologies which may be extracted from images captured by image capturing device from a perspective of a distal end of a medical device as the medical device moves through a branched anatomical structure.

FIG. 22 illustrates a schematic of a medical device with optional position, orientation, roll, and insertion sensors as the medical device moves through a lumen of an anatomical structure.

FIG. 23 illustrates a Cartesian coordinate system associated with the optional position sensor of FIG. 22.

FIG. 24 illustrates an orientation angle associated with the optional orientation sensor of FIG. 22.

DETAILED DESCRIPTION

Figure 1:
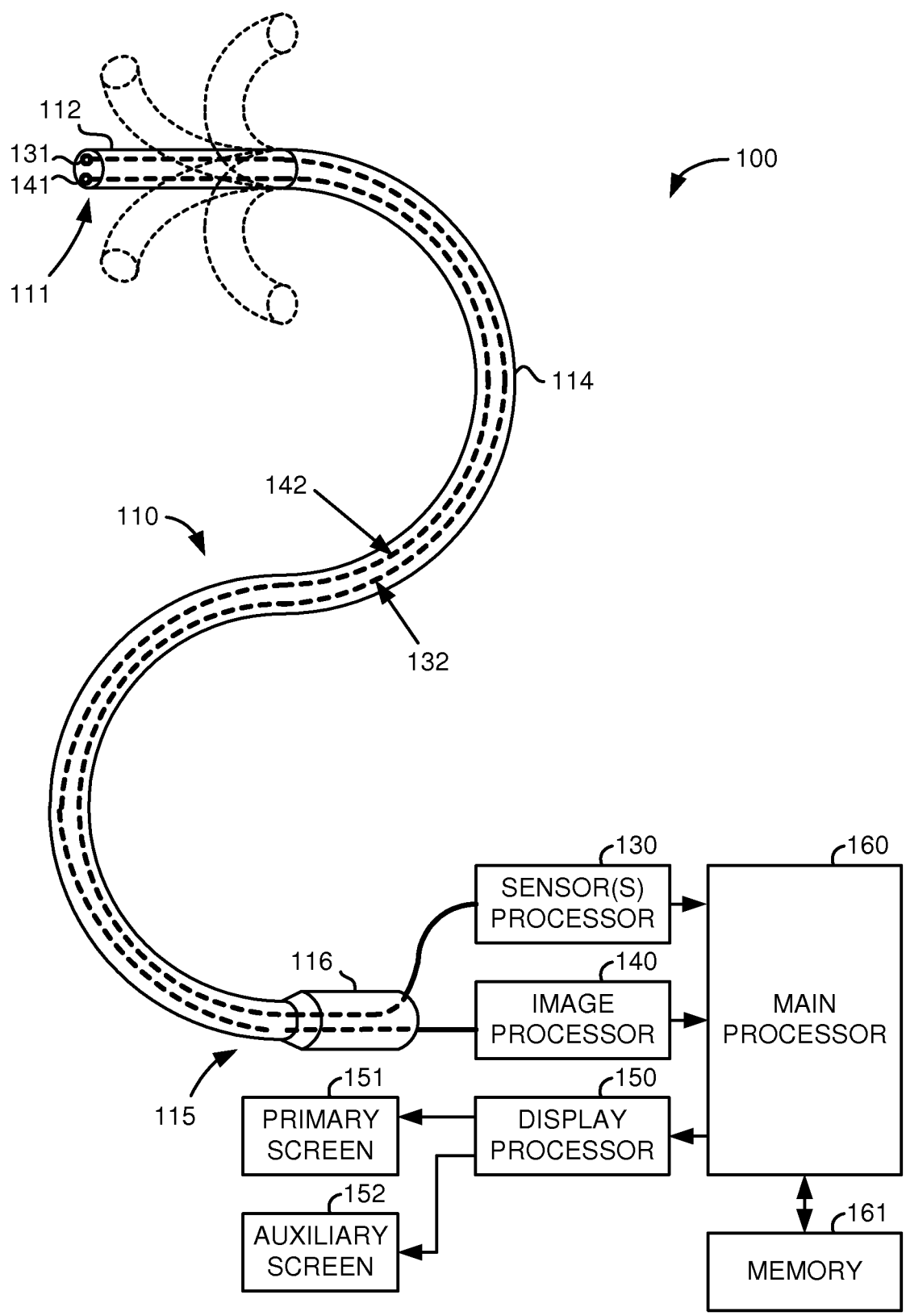
FIG. 1 illustrates a medical system, utilizing aspects of the present invention, which includes a hand-operated medical device.

FIG. 1 illustrates, as an example, a medical system 100 including a steerable medical device 110, one or more sensors 131, a sensor(s) processor 130, one or more signal communication cables 132 coupling the one or more sensors 131 to the sensor(s) processor 130, an image capturing element 141, an image processor 140, an optical fiber or electrical cable 142 coupling the image capturing element 141 to the image processor 140, a display processor 150, a primary display screen 151, an auxiliary display screen 152, a main processor 160, and memory 161. Although shown as separate units, the sensor(s) processor 130, image processor 140, display processor 150, and main processor 160 may be implemented in a single processor or their respective functions distributed among a plurality of processors, wherein each of such processors may be implemented as hardware, firmware, software or a combination thereof. As used herein, the term processor is understood to include interface logic and/or circuitry for translating and/or communicating signals into and/or out of the processor as well as conventional digital processing logic. The memory 161 may be any memory device or data storage system as conventionally used in computer systems. The primary and auxiliary display screens, 151 and 152, are preferably computer monitors capable of displaying three-dimensional images to an operator of the system 100. However, for cost or other considerations, either or both of the primary and auxiliary display screens, 151 and 152, may be a standard computer monitor capable of only displaying two-dimensional images.

The medical device 110 has a flexible body 114, a steerable tip 112 at its distal end 111, and a hand-operable handle 116 at its proximal end 115. Control cables (not shown) or other control means typically extend from the handle 116 to the steerable tip 112 so that the tip 112 may be controllably bent or turned as shown for example by dotted line versions of the bent tip 112. The medical device 110 may be an endoscope, catheter or other medical instrument having a flexible body and steerable tip.

The image capturing element 141 may be a stereoscopic or monoscopic camera or other imaging device disposed at the distal end 111 for capturing images that are transmitted to and processed by the image processor 140 and/or display processor 150 and displayed on the primary display screen 151, auxiliary display screen 152, and/or other display means according to the various aspects of the invention as described herein. Alternatively, the image capturing element 141 may be a fiber-optic bundle that couples to an imaging and processing system on the proximal end of the medical device 110, such as a fiberscope. The image capturing element 141 may also be single or multi-spectral that captures image data in the visible or infrared/ultraviolet spectrum. Thus, any image capturing element, device, or system referred to herein may be any one or a combination of these and other imaging technologies. One of a plurality of fiber optic cables (not shown) may be coupled at its proximal end to a light source (not shown) for illumination purposes at the distal end 111. Other of the plurality of fiber optic cables (not shown) may be configured with position and bend or shape sensors such as Fiber Bragg Gratings (or other strain sensors such as those employing Rayleigh scattering) distributed along the length of the medical device 110 so that light passing through these fiber optic cables is processed by the sensor(s) processor 130 to determine a current pose and shape of the medical device 110.

Figure 2:
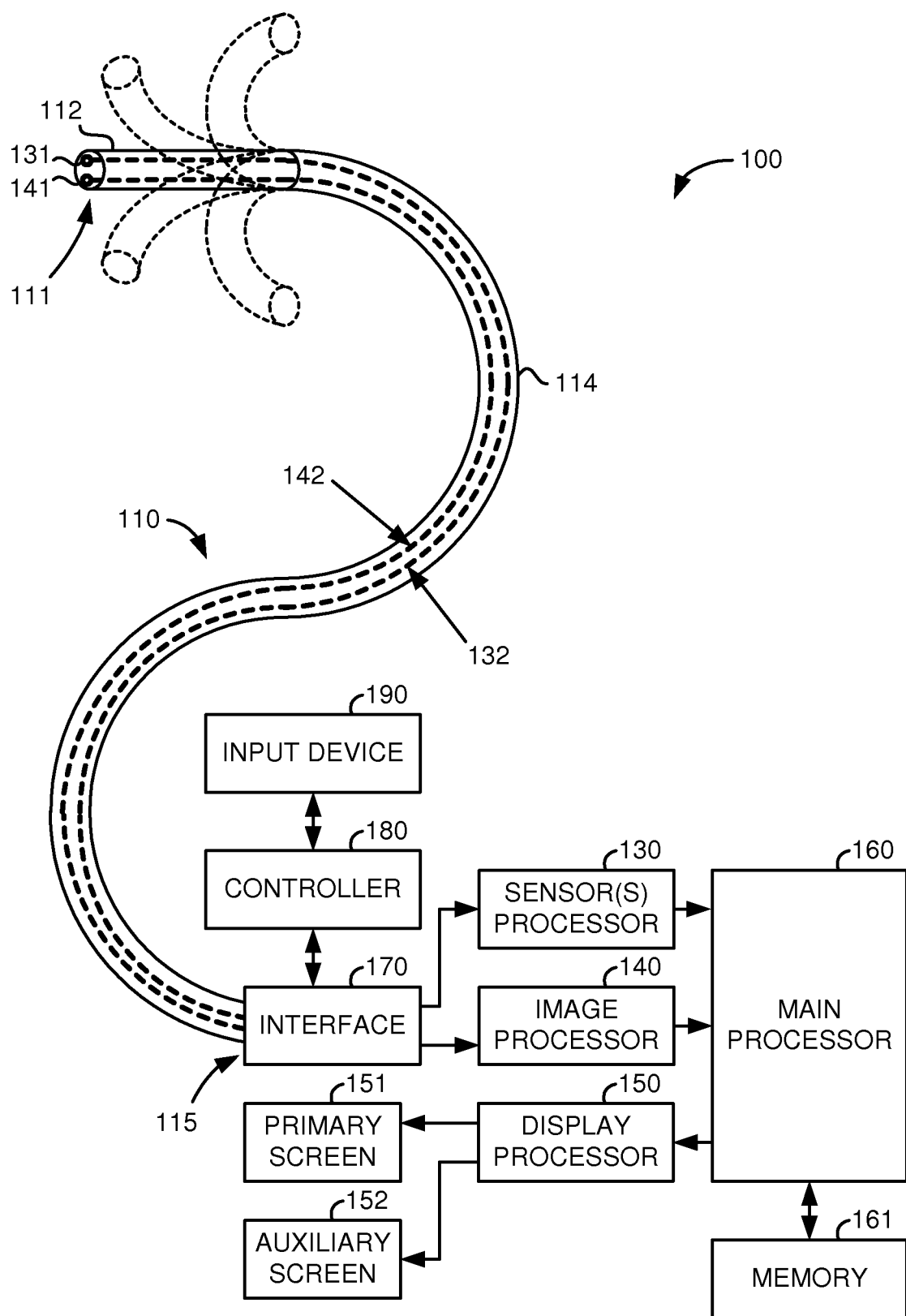
FIG. 2 illustrates an alternative medical system, utilizing aspects of the present invention, which includes a teleoperated medical device.

FIG. 2 illustrates, as an example, an alternative embodiment of the medical system 100 in which the handle 116 is replaced by an electromechanical interface 170, controller 180, and input device 190 for teleoperating the medical device 110. The interface 170 includes actuators for actuating cables in the medical device 110 to steer its tip 112 as well as an actuator for moving the entire medical device 110 forward and backward so that it may be inserted into and retracted out of a patient through an entry port such as a natural body orifice or a surgeon created minimally invasive incision. In addition, the interface 170 may include an actuator for rotating the medical device 110 about its central longitudinal axis. The controller 180 is preferably implemented as hardware, firmware or software (or a combination thereof) in the same one or more computer processors as the processors 130, 140, 150, and 160, or a different computer processor. The flexible body 114 may be passively or actively bendable. The medical system can also be a hybrid of the above two examples.

Examples of such steerable medical devices are described in U.S. 2010/0249506 A1 entitled "Method and System for Assisting an Operator in Endoscopic Navigation" and WO 2009/097461 A1 entitled "Apparatus and Methods for Automatically Controlling an Endoscope, which are each incorporated herein by reference. Details on the determination of the endoscope's position and bending using Fiber Bragg Gratings may be found, for examples, in U.S. 2007/0156019 A1 entitled "Robotic Surgery System Including Position Sensors Using Fiber Bragg Gratings", U.S. 2008/0212082 A1 entitled "Fiber Optic Position and/or Shape Sensing Based on Rayleigh Scatter", U.S. 2008/0218770 A1 entitled "Robotic Surgical Instrument and Methods using Bragg Fiber Sensors", and U.S. 2009/0324161 A1 entitled "Fiber Optic Shape Sensor", which are each incorporated herein by reference.

Figure 3:
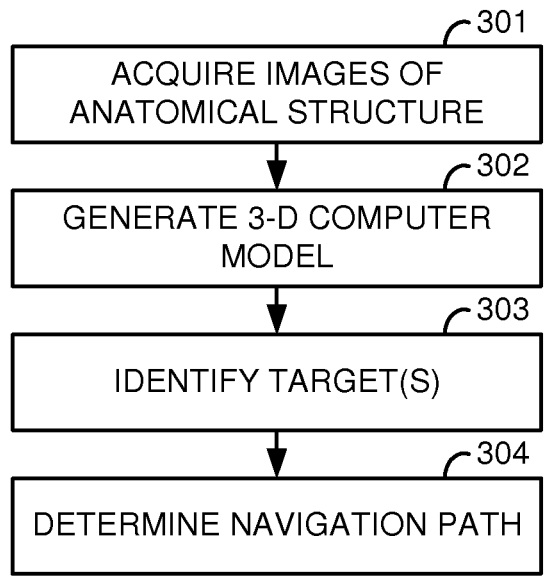
FIG. 3 illustrates a diagram of preoperative tasks conducted prior to performing a medical procedure on a patient.

FIG. 3 illustrates, as an example, a diagram of preoperative tasks that may be performed in planning a medical procedure to be performed on a patient. In the following example, the branched anatomical structure may move during a medical procedure as in the periodic motion of the air and blood circulatory systems or in a non-periodic motion such as a cough or other body spasm.

In block 301, a set of images of a patient is acquired using an appropriate imaging technology from which a three-dimensional (3-D) computer model of the branched anatomical structure may be generated. Examples of such an imaging technology include, but are not limited to, fluoroscopy, Magnetic Resonance Imaging, thermography, tomography, ultrasound, Optical Coherence Tomography, Thermal Imaging, Impedance Imaging, Laser Imaging, and nano-tube X-ray imaging. If the branched anatomical structure is subject to expansion/contraction cycles, such as the human lungs, it may be advantageous to acquire the set of images at an extremum using a triggering signal, such as from a respirator or motion detector.

In block 302, a three-dimensional (3-D) computer model of the branched anatomical structure is generated from the acquired images of the anatomical structure. In block 303, one or more targets may be identified in the branched anatomical structure. The targets are locations or objects in or adjacent to the anatomical structure where or upon which a medical procedure is to be performed. For example, the target may be a tumor in or adjacent to the anatomical structure. The target(s) may be identified by a surgeon or radiologist in a conventional manner by analysis of the acquired images of the anatomical structure or the generated 3-D computer model information, whichever is more convenient and/or reliable for such identification.

In block 304, a navigational path may be determined to and through the anatomical structure for the working end of the medical device 110 to travel to each target. In this case, the working end is assumed to be the distal end 111 of the medical device 110. The surgeon may determine a suitable navigational path to a target by analyzing the acquired images of the anatomical structure or the generated 3-D computer model so as to take into account any damage to the patient that the medical device 110 may cause as it moves towards the target as well as the shortest time and/or shortest path. Alternatively, a computer program may be executed by a processor to perform such analysis to determine the navigational path using artificial intelligence techniques.

Figure 4:
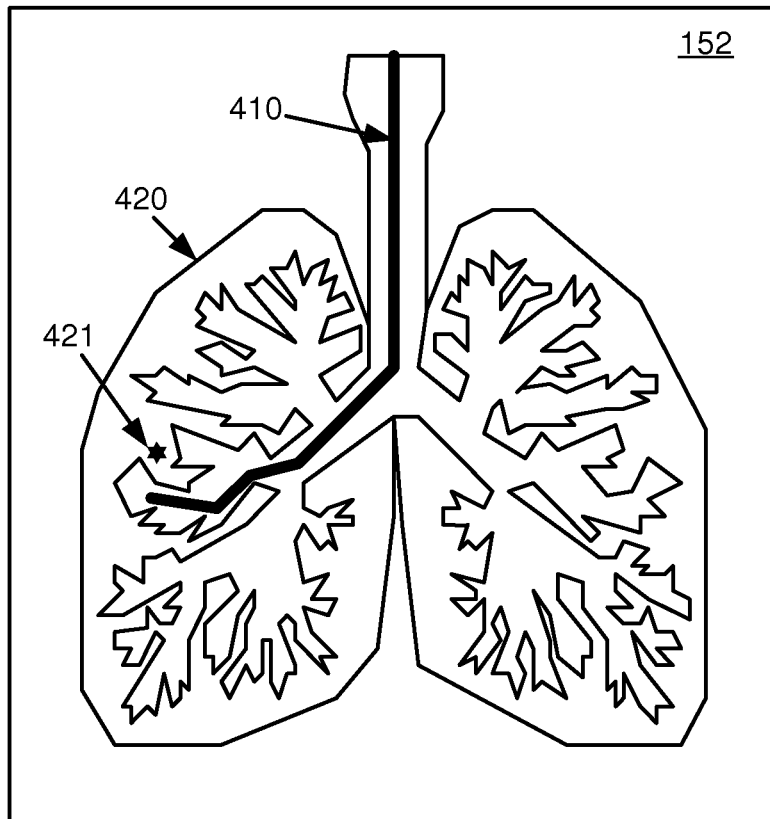
FIG. 4 illustrates a view of an auxiliary screen during navigation of a medical device to a target area in a branched anatomical structure.

FIG. 4 illustrates, as an example, a view of the auxiliary display screen 152 during navigation of the medical device 110 to a target area in an anatomical structure. The view may be either a 2-D or 3-D view of a computer model 420 of the branched anatomical structure and a computer model 410 of the medical device 110, which is updated in real-time as the medical device 110 moves through the anatomical structure. Also shown is an indication 421 of the target. Thus, the auxiliary screen 152 assists the surgeon to steer the medical device 110 through the anatomical structure to the target.

In this example, the branched anatomical structure is a pair of lungs having a plurality of natural body passages or lumens including a trachea, bronchi, and bronchioles. The medical device 110 is a bronchoscope and its entry port into the patient is the patient's mouth. Due to the nature of the lungs, the medical device 110 may be guided through a number of linked lumens or branches of the bronchial tree. In doing so, the flexible body 114 of the medical device 110 conforms to the passages through which it travels. Although a pair of lungs is shown in the present example, it is to be appreciated that the various aspects of the present invention are also applicable and useful for other anatomical structures such as the heart, brain, digestive system, circulatory system, and urinary system, in addition to the respiratory system.

In addition, or alternatively, to displaying computer models of the branched anatomical structure and medical device on the auxiliary display screen 152 as shown in FIG. 4, an image captured by the image capturing element 141 may be shown side-by-side on the primary display screen 151 with a synthetic image which is generated from the 3-D computer model of the branched anatomical structure from the perspective of the distal end 111 of the medical device 110. In this case, an arrow may be displayed on the synthetic image to indicate a direction to be taken towards the target. For additional details, see, for example, U.S. application Ser. No. 13/107,562 entitled "Medical system providing dynamic registration of a model of an anatomical structure for image-guided surgery," filed May 13, 2011, which is incorporated herein by reference.

A number of pre-operative registration tasks are performed in a conventional manner in preparation of performing a medical procedure on a patient using the system 100. First, the medical device 110 is localized to a fixed reference frame by, for example, touching the distal end 111 of the medical device 110 to one or more known and stationary points in the fixed reference frame. Second, the patient may be registered to the fixed reference frame by touching the distal end 111 of the medical device 110 to one or more points on the patient, which points correspond to identifiable points on the acquired images of the patient such as natural body features or artificial markers. Third, the computer model of an anatomical structure may be registered to the patient using corresponding reference points on the patient and the computer model such as natural body features or artificial markers. Thus, the medical device 110, branched anatomical structure, and computer model of the anatomical structure may be registered in this way to each other and to the fixed reference frame.

During the performance of a medical procedure on the patient, however, due in part to inherent inaccuracies in tracking the position of the distal end of the medical device 110 as it moves through the branched anatomical structure, registration errors may occur between the medical device and the computer model of the branched anatomical structure. The registration errors may result from errors in the kinematics used for tracking the distal end of the medical device 110, errors associated with the sensors used for tracking the position of the distal end, and/or errors caused by movement of the branched anatomical structure. As a result of these and other possible errors, misregistration of the branched anatomical structure to the medical device 110 may develop. As a consequence, the navigation guidance assistance provided by the system may be in error.

Figure 5:
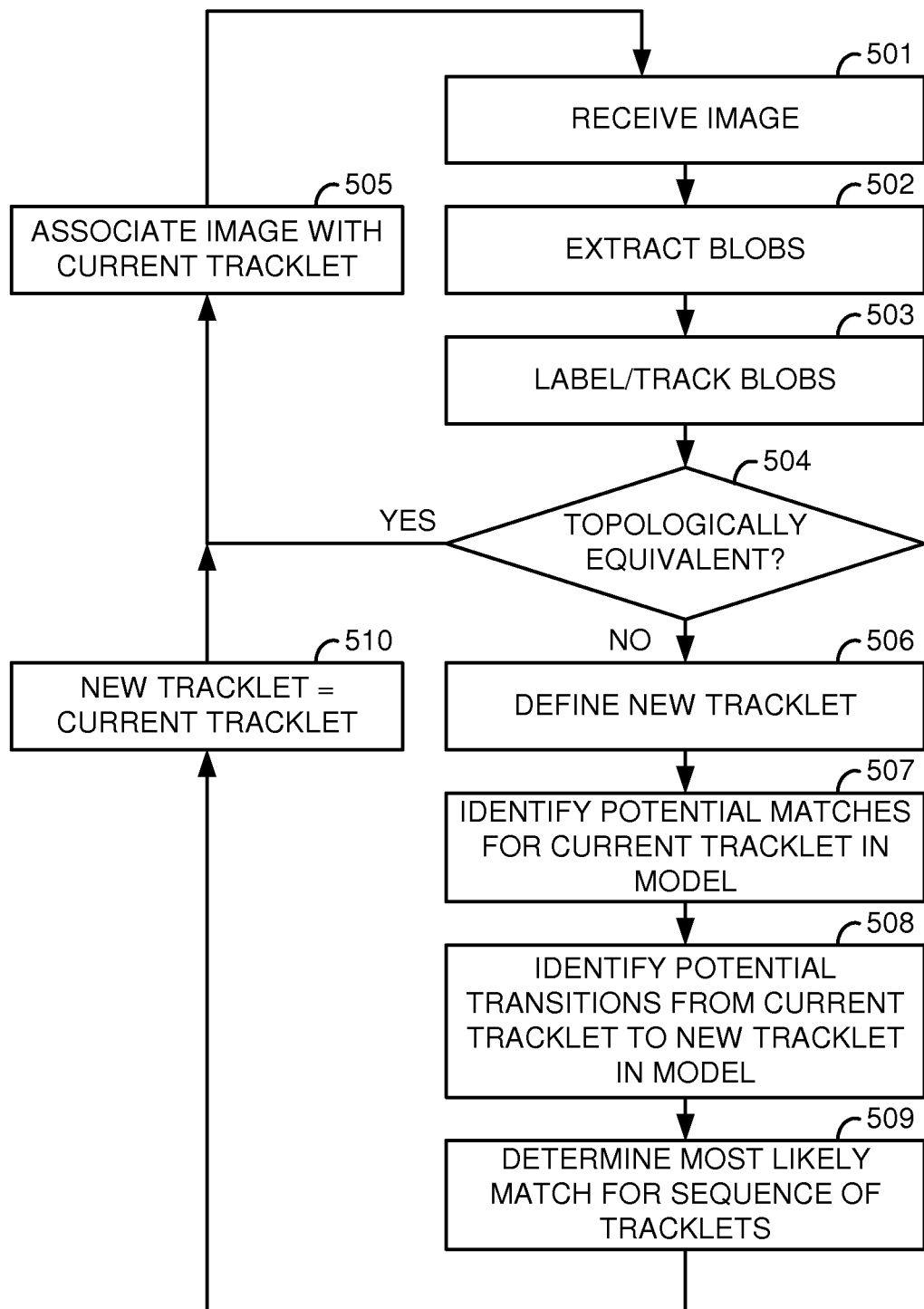
FIG. 5 illustrates a flow diagram of a method for registering a computer model of a branched anatomical structure to a medical device for determining a position of the medical device in the branched anatomical structure, utilizing aspects of the present invention.

FIG. 5 illustrates, as an example, a method, which is preferably implemented by the main processor 160, for registering a computer model of a branched anatomical structure to a medical device so that a position of the medical device in the branched anatomical structure may be determined as the medical device moves through the branched anatomical structure. In this case, the position of the medical device in the branched anatomical structure indicates the lumen of the branched anatomical structure that the medical device is currently in. The method may be used as a standalone registration technique or it may be combined with other registration techniques. For example, the method may be used for global registration and another technique used for local registration.

In brief, the method identifies, tracks, and correlates lumen information that is extracted from images captured from the perspective of a distal end of the medical device as the medical device moves through the branched anatomical structure with corresponding lumen information extracted from the computer model of the branched anatomical structure to enable registration of the distal end of the medical device to the branched anatomical structure. In particular, the method compares information of topologies, feature attributes, behaviors, and/or relationships of lumens seen in a sequence of captured images with corresponding information of topologies, feature attributes, behaviors, and/or relationships of lumens in the computer model of the branched anatomical structure. A most likely match between a path of lumens seen in the sequence of captured images and a path of lumens in the computer model of the branched anatomical structure is then determined to indicate which lumen of the branched anatomical structure the medical device is currently in.

In a first part of the method, comprising blocks 501-504, blobs are extracted, labeled and tracked in sequentially received images until a change occurs in the set of blobs appearing in the images. Each extracted blob is extracted so as to indicate a currently entered or enterable lumen in the branched anatomical structure. For example, lumens in the captured image presumably appear as darker holes in the image due to the fact that the further side of the lumen is less illuminated. Image processing techniques can then be used to extract the salient dark regions in the image. These extracted salient dark regions are thus referred to herein as "blobs". Because the extracted blobs indicate lumens, the terms blob and lumen may be used interchangeably herein. A sequence of images that are topologically equivalent (e.g., a sequence in which the same set of blobs or lumens appears) is referred to herein as a "tracklet". Thus, the path that the medical device moves through the branched anatomical structure is a sequence of tracklets.

Figure 6:
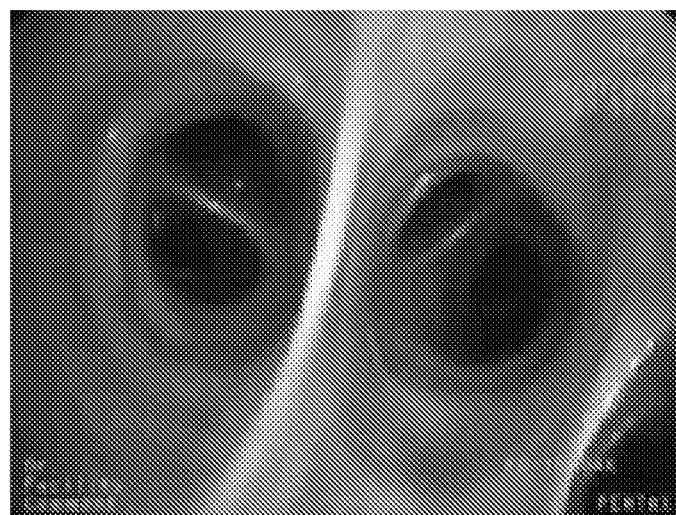
FIG. 6 illustrates an image captured by image capturing device from a perspective of a distal end of a medical device as the medical device moves through a branched anatomical structure.

In block 501, the method receives an image that has been captured, for example by the image capturing element 114, from the perspective of the distal end of the medical device as the medical device moves through the branched anatomical structure. An example of such a received image is shown in FIG. 6 in which a bifurcation in the lungs is shown and downstream bifurcations appear in each of the lumens of the bifurcation. The received image may be a monoscopic image (as shown) or a stereoscopic image providing depth information.

Figure 7:
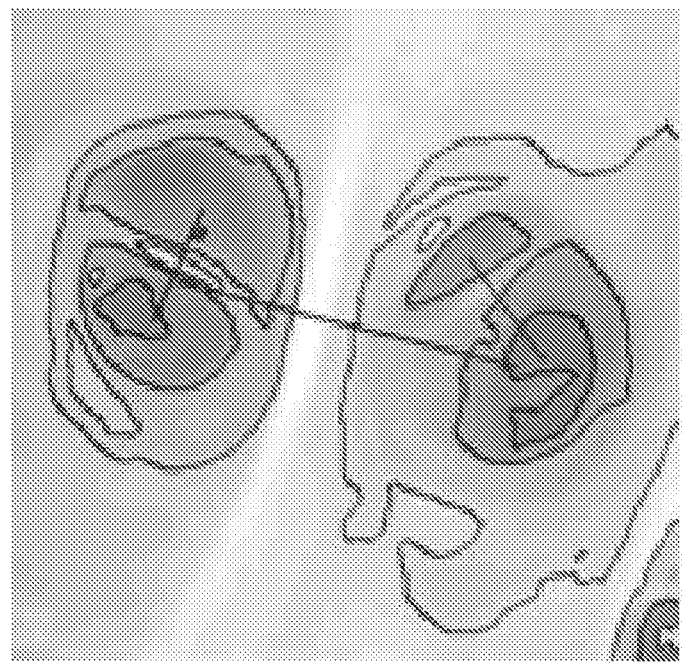
FIG. 7 illustrates blobs extracted from the captured image of FIG. 6 along with line segments useful for defining feature attributes for the blobs.

In block 502, the method processes the received image to extract blobs using any suitable one of a number of well known blob detection algorithms such as Maximally Stable Extremal Regions (MSER). An example of a processed image is shown in FIG. 7 in which the coarse outlines of blobs extracted from the received image of FIG. 6 appear. Also shown in FIG. 7 is a line segment for each bifurcation which has one end connected to the centroid of one lumen and the other end connected to the centroid of the other lumen of the bifurcation.

To better define the blobs as closed curves that are indicative of lumens in the branched anatomical structure, additional image processing may be desirable using well known image filtering and/or edge detection techniques before and/or during blob extraction. Lens distortion correction may also be performed to help the association of the image observation in the captured images with the computer model of the branched anatomical structure. FIGS. 8-20 illustrate various blob topologies that may result from such processing.

For example, FIG. 8 illustrates the medical device moving through a lumen 801 where no downstream node is visible at the time. FIG. 9 illustrates an example of the medical device moving through a lumen 901 where a downstream bifurcation comprising lumens 902, 903 is visible. FIG. 10 illustrates an example of the medical device moving through a lumen 1001 where a downstream trifurcation comprising lumens 1002, 1003, 1004 is visible. FIG. 11 illustrates another example of the medical device moving through a lumen 1101 where a downstream trifurcation comprising lumens 1102, 1103, 1104 is visible at a different orientation than the trifurcation of FIG. 10. FIGS. 12 and 13 illustrate a sequence of images. FIG. 12 illustrates an example of the medical device moving through a lumen 1201 where a first downstream bifurcation comprising lumens 1202, 1203 is visible and a second downstream bifurcation comprising lumens 1204, 1205 is visible within the lumen 1203. FIG. 13 illustrates an example of the medical device having moved into lumen 1203 so that lumens 1201, 1202 are no longer visible.

In block 503, each of the extracted blobs is tracked. If the blob is being seen for the first time in the current sequence of images being received by looping through blocks 501-504, then it is labeled with a previously unassigned reference number so that the method may keep track of the blob (or more particularly, the lumen that the blob indicates). On the other hand, if the blob was seen in a previously received image, then it has already been assigned a label and it is tracked instead. Tracking in this context means identifying the blob from one image to another. Generally, such identification may be simply made by taking into account the relative positions that blobs appear in the images.

Figure 18:
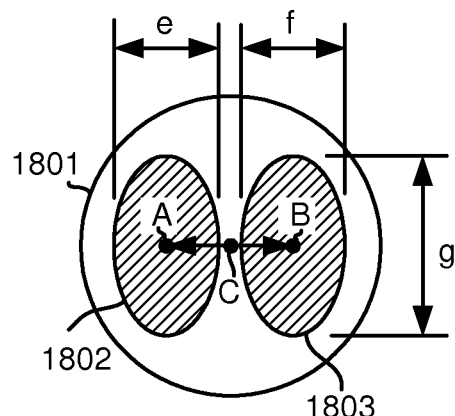
FIGS. 18-19 illustrate an example of a sequence of blobs extracted from images captured by image capturing device from a perspective of a distal end of a medical device as the medical device moves towards a bifurcation in a branched anatomical structure.
Figure 19:
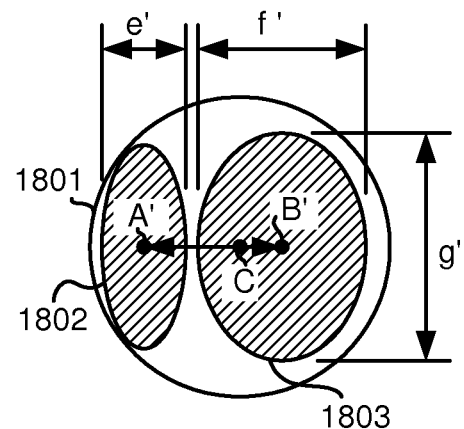

As an example of blob tracking, FIGS. 18 and 19 illustrate two sequential images in a tracklet. In FIG. 18, a bifurcation comprising blobs/lumens 1802, 1803 is seen from a distance while the medical device is moving through a lumen 1801 towards the bifurcation. In FIG. 19, the same bifurcation is seen from a closer distance as the medical device has moved through the lumen 1801 with its distal end being steered towards blob/lumen 1803. In this example, blobs 1802, 1803 may be easily tracked between the images shown in FIGS. 18 and 19, because their positions relative to each other remain the same (i.e., blob 1802 continues to be the left lumen of the bifurcation and blob 1803 continues to be the right lumen of the bifurcation).

As another slightly more complicated example of blob identification, previously described FIGS. 12 and 13 illustrate a different pair of sequential images resulting in a transition between adjacent tracklets. By comparison of FIGS. 12 and 13, it is most probable that in FIG. 13, the medical device has moved into one of the lumens 1202, 1203 since the total number of lumens (i.e., blobs) has decreased. Further, it is most probable that the medical device has moved into lumen 1203. This is because a downstream bifurcation is visible in FIG. 13 and a downstream bifurcation is only visible in lumen 1203 according to the earlier received image shown in FIG. 12.

In block 504, the method makes a determination whether topological equivalence is maintained in the current sequence of images being received as the method loops through blocks 501-504. If the determination in block 504 is a YES, then in block 505, the method associates the received image with the current tracklet and loops back to block 501 to add to the current sequence of images. On the other hand, if the determination in block 504 is NO, then in block 506, a new tracklet is defined starting with the most recently received image. The current tracklet is then closed so that it includes only the current sequence of images up to, but not including the most recently received image (i.e., the image first showing a change in the set of blobs by a labeled blob disappearing or a new blob appearing).

As an example, a current tracklet may result in extracted blobs as shown in FIG. 12. After the medical device moves into lumen/blob 1203, a new tracklet would then result in extracted blobs as shown in FIG. 13.

When the number of blobs decreases between a pair of sequential images, a primary assumption is the medical device has passed by a node (e.g., bifurcation or trifurcation) and entered into a lumen branching out from the node, such as described in reference to FIGS. 12 and 13. On the other hand, when the number of blobs increases between a pair of sequential images, the primary assumption is the medical device has moved forward in a lumen to a point where a downstream node, such as a bifurcation or trifurcation, is visible. These primary assumptions may be refuted by knowledge of the progression of the tracked blobs in sequential images and/or sensor data. For example, a disappearing blob approaching towards and exiting from a boundary of the image in a progression of sequentially captured images affirms the primary assumption that the medical device has passed a node, whereas a different behavior of a disappearing blob in the sequence of images may refute the primary assumption. As another example, a sensor capable of sensing the insertion and retraction of the medical device into and out of the branched anatomical structure can refute the primary assumption with a contrary indication.

Figure 14:
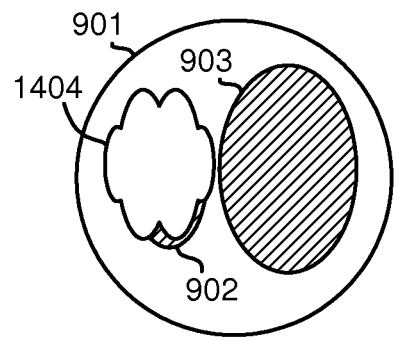
FIG. 14 illustrates an example of a false negative blob identification for an image captured by image capturing device from a perspective of a distal end of a medical device as the medical device moves through a branched anatomical structure.
Figure 15:
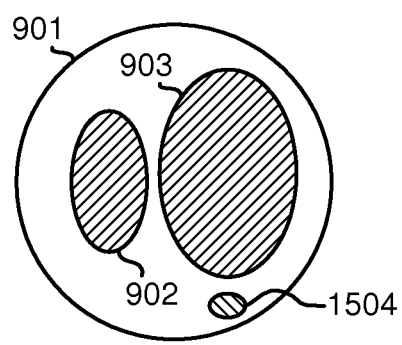
FIG. 15 illustrates an example of a false positive blob identification for an image captured by image capturing device from a perspective of a distal end of a medical device as the medical device moves through a branched anatomical structure.

One potential problem with such primary assumptions is the determination of false negatives (i.e., an incorrect determination that the number of blobs/lumens in the current image is less than the number of blobs/lumens in the prior image) and false positives (i.e., an incorrect determination that the number of blobs/lumens in the current image is more than the number of blobs/lumens in the prior image). Using FIG. 9 as a basis for an example of a false negative as shown in FIG. 14, an obstruction 1404 blends in so well with background tissue that it appears the blob 902 behind it has disappeared. Again using FIG. 9 as a basis for an example of a false positive as shown in FIG. 15, a foreign object 1504 appears within the lumen 901.

Depending upon the type and cause of such false negatives and positives, additional processing and/or logic may be performed by the method to eliminate false determinations. For example, a single downstream blob/lumen positioned off to one side as shown in FIG. 14 seems unlikely, so the false negative should be ignored. As another example, although three blobs/lumens indicating a trifurcation may appear as shown in FIG. 15, a comparison of feature attributes for the extracted blobs with corresponding feature attributes for trifurcation blobs in synthetic images generated from the computer model of the branched anatomical structure may expose a false positive determination in the current image. In addition to blob topologies and/or characteristics that are inconsistent with those expected from the computer model of the branched anatomical structure, a requirement for temporal consistency between successive images may also expose false negatives and positives. False negatives and positives resulting from backing up the medical device and going forward again may also be detected by analyzing successive images. As an example of backing up and going forward again, if the right lumen of a bifurcation gradually disappears in successive images to the right of the field of view resulting in a single lumen being seen, then a second lumen gradually appears in successive images from the right of the field of view, this may indicate a situation where the medical device has first gone into the left lumen of the bifurcation, then backed out of the left lumen so that the right lumen of the bifurcation is once again visible.

In the second part of the method, comprising blocks 507-510, the current sequence of images (i.e., the current tracklet) is processed and a most likely match with a path of lumens in the computer model of the branched anatomical structure is determined by taking into account the current tracklet and its adjacent tracklets. There are a number of potential paths that the medical device may take as it moves through lumens of the branched anatomical structure. Each tracklet identified in the first part of the method may correspond to a different lumen of the branched anatomical structure. Thus, a sequence of tracklets which have been identified by looping through blocks 501-510 as the medical device moves through the branched anatomical structure provide a pictorial history of images captured as the medical device moves along a path in the branched anatomical structure. Each time a new tracklet is identified, it is added to the sequence of tracklets and the updated sequence of tracklets is matched against the potential paths that the medical device may take as it moves through lumens of the branched anatomical structure. It may happen that two or more potential paths are close matches to the updated sequence. In that case, although the closest match may be designated the most likely match up to that point, when a next tracklet is identified after looping back through blocks 501-504, the updated sequence of tracklets may match more closely with one of the other potential matches to indicate a "true" match versus the previously identified "false" match. Thus, a "false match" error is self-corrected in the method. In contrast, prior art methods generally require the operator to recognize when a "false match" has occurred and to correct the error, which may be very difficult and time consuming for the operator.

In block 507, the method identifies potential matches of the current tracklet with locations within the computer model of the branched anatomical structure. Although the current tracklet is not limited to being a tracklet which has ended by the medical device passing through a node of the branched anatomical structure by moving through one lumen leading up to the node and entering into another lumen branching out from the node, this type of tracklet is commonly encountered and will be used for describing the method.

The potential matches represent a limited set of nodes (e.g., bifurcations and trifurcations) from the universe of all nodes in the branched anatomical structure. Numerous filtering criteria may be used to limit the set of nodes (e.g., by identifying potentially matching nodes or by ruling out certain nodes). One such filtering criterion is topological equivalence between the current tracklet and potential matches of synthetic images which may be generated from the computer model of the branched anatomical structure. The synthetic images represent views within the three-dimensional computer model of the branched anatomical structure that correspond to images captured at the distal end of the medical device as it moves through the branched anatomical structure. Although such synthetic images are described as being used herein, it is to be appreciated that information indicative of such synthetic images may be extracted instead from the computer model. As an example of using topological equivalence as a filtering criterion, if the tracklet indicates the node being passed is a bifurcation, then only bifurcation nodes may be included. Conversely, if the tracklet indicates the node being passed is a trifurcation, then only trifurcation nodes may be included. As another example, if the tracklet indicates that a downstream node is visible through one of the lumens of an upstream node, then only synthetic images indicating nodes satisfying such a topology may be included in the set of potential matches. Topological equivalence is preferably a threshold requirement for a synthetic image to be considered as a potential match to the tracklet.

Other filtering criteria for limiting the set of nodes to generate potential matches with the current tracklet may use available sensor information. As an example, FIG. 22 illustrates a schematic diagram in which the medical device 110, as controlled by interface 170, moves through an opening 2201 and along a curved path 2202 in an anatomical structure represented by block 2200. Four optional sensors 2221, 2222, 2223, 2224 provide information that may be employed to further limit the set of potential node matches. Signal communication cables or lines 132 transfer information from the distal end sensors 2222, 2223 back to the interface 170. As shown in FIG. 1, the sensor information is then provided to a sensor(s) processor 130, which may include an analog-to-digital (A/D) converter, so that the information may be converted into a form suitable for processing by the main processor 160.

An insertion sensor 2221 may optionally be provided to provide information on how much the medical device has been inserted into the anatomical structure 2200. With this information, only nodes within a threshold distance to an insertion depth from the opening will be included in the set of potential matches. This type of sensor is especially useful for detecting a direction reversal situation, such as when a medical device has backed out of a bifurcation lumen after previously entering the lumen. Typically, such an insertion sensor 2221 may conventionally be provided in or adjacent to the interface 170 to detect linear movement of the medical device 110 into and out of the anatomical structure 2200.

A position sensor 2222 may optionally be provided at the distal end 111 of the medical device 110 to provide position information in three-dimensional space (such as point $X_K$, $Y_K$, $Z_K$ illustrated in FIG. 23). With this information, only nodes within a threshold distance (such as within an uncertainty range of the sensor) from the sensed position will be included in the set of potential matches.

An orientation sensor 2223 may optionally be provided at the distal end 111 of the medical device 110 to provide orientation information for the distal end. For example, as illustrated in FIG. 24, information of an angle φ indicating how much a line 2411 corresponding to the horizontal line of the received image (which has been captured within lumen 2413) deviates from a reference line 2412 that is perpendicular to a gravity vector may be provided by the orientation sensor 2223. With this information, orientations of blobs in the received images may be adjusted to more accurately reflect what they are expected to look like in synthetic images generated from the computer model of the branched anatomical structure. This orientation information is particularly useful to prevent possible errors in determining which of the blobs is to the left or to the right of the other (i.e., avoidance of left/right reversal errors) since there will only be one way to associate a two-lumen bifurcation.

A roll sensor 2224 may optionally be provided to provide information of how much the medical device 110 has been rotated about its longitudinal axis. This information may be useful to estimate an orientation of the distal end when an orientation sensor is unavailable. Typically, such a roll sensor 2224 may conventionally be provided in or adjacent to the interface 170 to detect rotation of the medical device 110 about its longitudinal axis.

In other embodiments, additional filtering data can include historical user inputs that can used to narrow the universe of node possibilities. For example, navigation control inputs (e.g., steering commands at one or more nodes) can be used as basis for identifying the most likely lumen(s) entered at a given node(s). This directional indication(s) can supplement or be used in place of blob tracking techniques, for example to enhance path tracking/lumen identification. Alternatively, a user can provide inputs specifically for node filtering purposes (e.g., specific anatomic features such as lumens, bifurcations, and/or other tissue structures can be manually "marked", labeled, or otherwise identified by the user for subsequent incorporation into the node filtering algorithm). This manual identification of anatomical landmarks can significantly reduce the range of node possibilities.

Quantitative comparisons may then be performed on the remaining members of the set after filtering the set of potential matches using a topological equivalence criterion and optionally, any available sensor information and/or user inputs. One technique for performing such quantitative comparisons uses feature attributes determined from the current tracklet and corresponding feature attributes extracted from the computer model of the anatomical structure for nodes of the computer model. As an example, feature attributes of the current tracklet should be reasonably close to feature attributes of synthetic images corresponding to the nodes of the computer model in order for the nodes and their synthetic images to be included in the set of potential matches. Since feature attributes may change as the distal end of the medical device is steered towards and through one of the lumens branching out from the node, feature attributes for the current tracklet are preferably determined from images captured prior to such distal end steering taking place.

To perform such quantitative comparisons between the tracklet and the potential matches, the method determines feature attributes for blobs in the current tracklet. The feature attributes are used to distinguish different bifurcations from one another and different trifurcations from one another in the branched anatomical structure.

Figure 16:
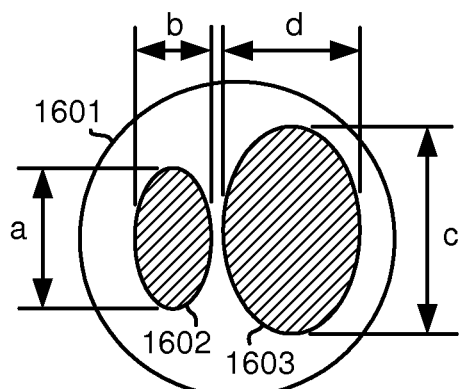
FIGS. 16-17 illustrate examples of blob characteristics which may be used to define feature attributes of blobs extracted from images captured by image capturing device from a perspective of a distal end of a medical device as the medical device moves through a branched anatomical structure.

As an example, FIG. 16 illustrates a bifurcation having left and right blobs/lumens 1602, 1603 as seen in blob/lumen 1601. Measurements of the heights, "a" and "c", and widths, "b" and "d", of the left and right lumens may be made according to a common scale (such as pixels in the received image) and ratios calculated to determine feature attributes, such as the ratio of heights, "a/c", the ratio of widths, "b/d", aspect ratio for the left blob/lumen, "b/a", and aspect ratio for the right blob/lumen, "d/c". As may be appreciated, the aspect ratios in particular may be very informative since they may indicate an angle at which the lumen extends away from the node.

Figure 17:
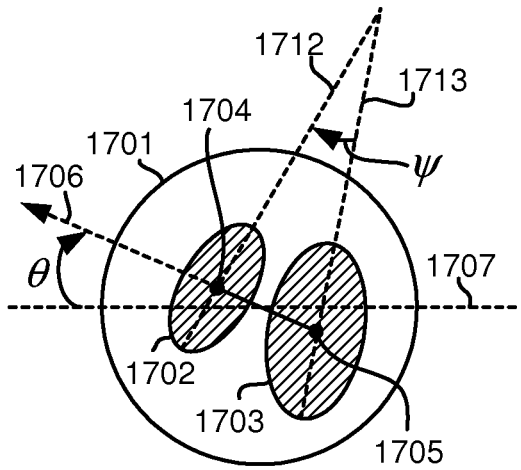

As another example, FIG. 17 illustrates a bifurcation having left and right blobs/lumens 1702, 1703 as seen in blob/lumen 1701. As a reference line, a horizontal line 1707 on a fixed horizontal plane (i.e., a plane perpendicular to a gravity vector) is shown. Another line 1706 is shown which extends through centroids 1704, 1705 of the blobs/lumens 1702, 1703. An angle, θ, may then be measured or otherwise determined between lines 1707, 1706 to serve as a feature attribute of the bifurcation. The length of the line segment connecting the centroids 1704, 1705 may also be used for generating other feature attributes of the bifurcation. For example, ratios may be calculated by dividing the heights and widths of each blob by the length of the line segment. An angle, w, may also be measured or otherwise determined between height lines 1712, 1713 of blobs 1702, 1703 to serve as another feature attribute of the bifurcation. A similar angle may also be measured or otherwise determined between width lines of the blobs to serve as yet another feature attribute of the bifurcation.

Figure 20:
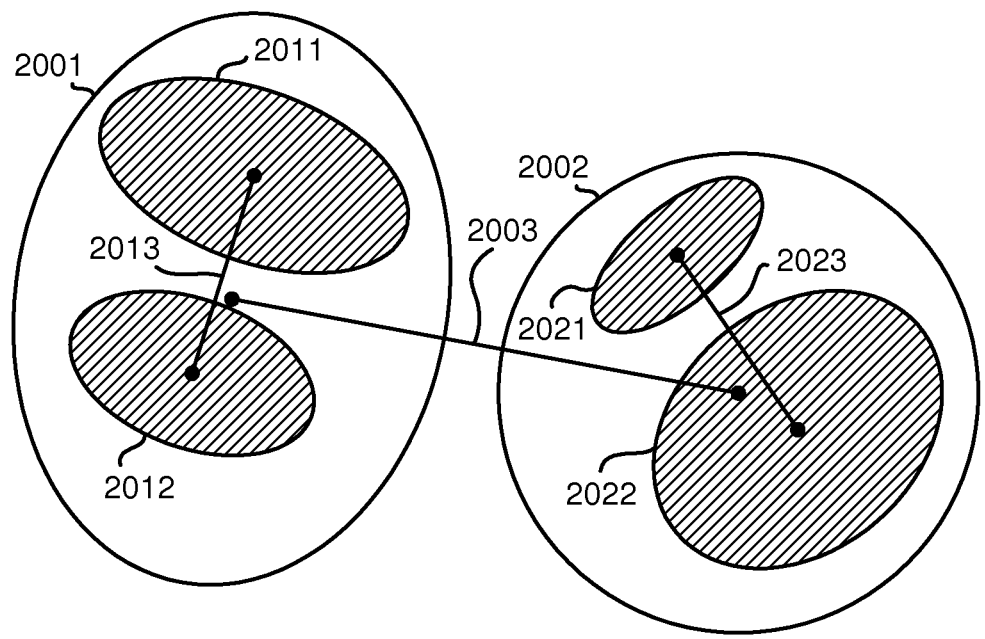
FIG. 20 illustrates blobs extracted from the captured image of FIG. 6 along with line segments used for defining feature attributes for the blobs.

As another example, FIG. 20 illustrates blobs extracted from the received image shown in FIG. 6. The extracted blobs in this case may result from additional image processing of the blobs shown in FIG. 7. A foreground bifurcation includes blobs/lumens 2001, 2002. Looking into blob/lumen 2001, a downstream bifurcation including blobs/lumens 2011, 2012 is seen. Likewise, looking into blob/lumen 2002, another downstream bifurcation including blobs/lumens 2021, 2022 is seen. A line segment 2003 connects the centroids of blobs/lumens 2001, 2002, a line segment 2013 connects the centroids of blobs/lumens 2011, 2012, and a line segment 2023 connects the centroids of blobs/lumens 2021, 2022. Several feature attributes may be defined and quantified using the line segments 2003, 2013, 2023. For example, the length of each line segment may used in a ratio with heights and/or widths of their respective blobs to define feature attributes for the blobs. As another example, angles between pairs of line segments may define other feature attributes of the image. Note that measurements of these feature attributes are orientation independent (i.e., result in the same values even if the image capturing device is rotated so as to change the orientation of the view). Thus, feature attributes of this kind are advantageous over orientation dependent feature attributes such as shown in FIG. 17 which require a fixed reference line.

Figure 21:
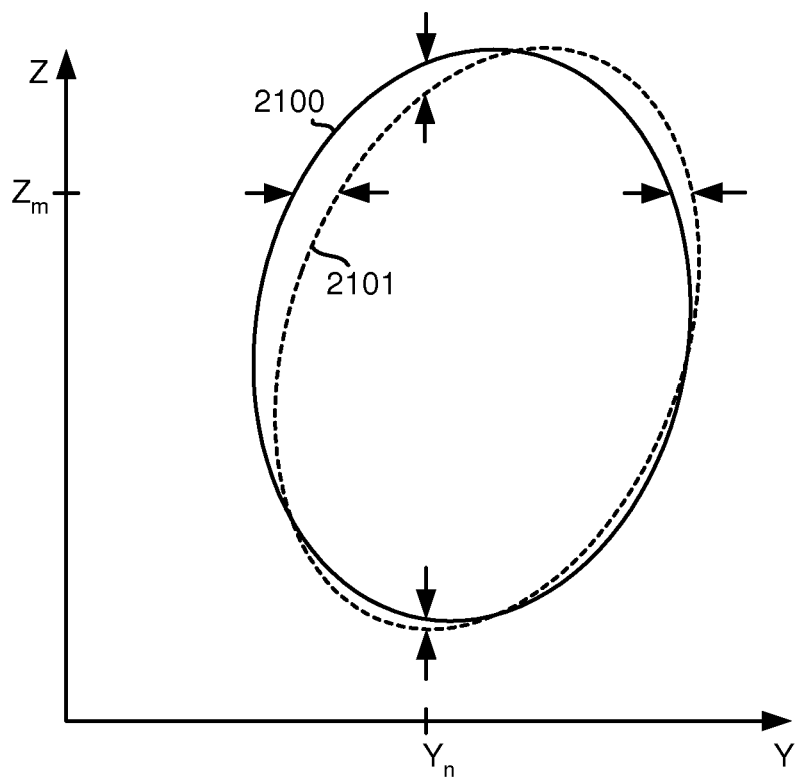
FIG. 21 illustrates a captured image blob whose shape is a feature attribute being used as a template to find matching blobs from synthetic images generated from a computer model.

As still another example, FIG. 21 illustrates the use of an extracted blob as a template to be compared with corresponding blobs of synthetic images generated from the computer model of the branched anatomical structure (e.g., shape of left blob/lumen of bifurcation in captured image compared to shape of left lumen in synthetic image of a bifurcation from the computer model of the branched anatomic structure). In this way, blob templates may also be used as feature attributes. As may be appreciated, many feature attributes beyond those described herein may also be defined using various lines and angles which are indicative of the relative shapes, sizes, and orientations of the extracted blobs. Further, rather than determining the feature attributes of extracted blobs for only one received image, the feature attributes may be determined for the tracklet (i.e., sequence of topologically equivalent images) by averaging the determined information and/or eliminating outliers in the determined information for the images in the tracklet. In addition to feature attributes determined from topological and geometrical features of extracted blobs as described above, other feature attributes may be defined and used in the methods described herein which are related to feature points identified in captured images. As an example, a scale invariant feature transform (SIFT) may be used to extract feature points from the captured images. The feature attributes used to compare the real image and the computer model can also be three-dimensional features extracted from multiple image frames using Structure from Motion (SfM) techniques. See, e.g., Richard Hartley and Andrew Zisserman, Multiple View Geometry in Computer Vision, Cambridge University Press, $2^{nd}$ Edition, 2004. Also, see, e.g., C. Tomasi and T. Kanade, "Factoring image sequences into shape and motion," Proceedings of the IEEE Workshop on Visual Motion, pages 21-28, Princeton, N.J., October 1991.

In addition to using feature attributes to distinguish bifurcations and trifurcations in a branched anatomical structure, feature attributes determined for a sequence of images may also be used for detecting false negatives and false positives as part of performing block 504. As an example, FIGS. 18 and 19 illustrate a sequence of images in which the image shown in FIG. 18 is received prior to the image shown in FIG. 19. As the distal end of the medical device is steered towards the right lumen 1803, the aspect ratio of the left lumen is expected to get smaller while the aspect ratio of the right lumen is expected to get larger. Other feature attributes may also be defined to indicate the direction of steering. For example, if the centroid of the blob/lumen 1802 is "A", the centroid of the blob/lumen 1803 is "B" and the centroid of the lumen 1801 through which the medical device is currently moving through is "C", then as the distal end of the medical device is steered towards the right lumen 1803, the distance between the centroids of blobs/lumens 1801, 1803 is expected to get smaller. Thus, by tracking the distances between the centroids, A and B, of the blobs/lumens 1802, 1803, to the centroid, C, of the lumen 1801, the direction that the distal end of the medical device is being steered may be determined. This information may be used to avoid false negatives as described above.

The quantitative comparisons performed by the method in block 507 indicate how "close" the feature attributes of blobs in the current tracklet match corresponding feature attributes of blobs in synthetic images of the potential node matches. As an example, a difference between the aspect ratio of the left blob of a bifurcation in the current tracklet and the aspect ratio of the left blob of a bifurcation in each of the synthetic images of the potential matches may be calculated. As another example, as shown in FIG. 21, differences (e.g., distances between opposing arrows at $Z_m$ and $Y_n$) between the shape of an extracted blob 2100 and a synthetic blob 2101, which has been generated from the computer model of the branched anatomical structure, may be determined and used for quantitative comparison purposes. The lower the difference in this case, the better the match between the tracklet and the node being represented in the synthetic image.

The quantitative comparisons are preferably converted to a probability or confidence score for each potential match or hypothesis. As an example, a likelihood of a $j^{th}$ hypothesis ($h_{i,j}$) for the $i^{th}$ tracklet ($t_i$) may be expressed as follows:

$$Pr(O_i|t_i=h_{i,j})=Pr(O_i^{(I)}|t_i=h_{i,j})Pr(O_i^{(S)}|t_i=h_{i,j}) \quad (1)$$

where $O_i$ represents all the observations associated with $t_i$; $O_i^{(I)}$ represents all image observations associated with $t_i$; and $O_i^{(S)}$ represents all available sensor observations associated with $t_i$.

After determining the quantitative comparisons for each of the members in the set of potential matches, the method stores the results of the quantitative comparisons for the current tracklet in a memory such as memory 161.

In block 508, the method identifies potential matches for the transition between the current tracklet to the new tracklet. Similar filtering techniques as described in block 507 may be performed in block 508. For example, a synthetic image corresponding to a view within a lumen may be generated from the computer model of the branched anatomical structure for each lumen in the branched anatomical structure. Captured images associated with the current tracklet and the next tracklet may then be compared with pairs of synthetic images corresponding to pairs of connected lumens within the branched anatomical structure for topological equivalence. Available sensor information may also be used to eliminate pairs of connected lumens within the branched anatomical structure from the set of potential matches for the transition between the current and new tracklets. Quantitative comparisons are then performed on the remaining members of the set of potential matches and preferably converted to a transition probability or confidence score for each potential match or hypothesis.

After determining the quantitative comparisons for each of the members in the set of potential transition matches, the method stores the results of the quantitative comparisons for the transitions from the current tracklet to the new tracklet in a memory such as memory 161.

In block 509, the method then determines a most likely match for the sequence of tracklets resulting from looping through blocks 501-510 by taking into account information of one or more adjacent tracklets in the sequence of tracklets making up the path of the medical device as it moves through the branched anatomical structure. Information of prior tracklets has been stored in the memory during the processing of blocks 507 and 508 for those tracklets while looping through blocks 501-510.

The likelihood of a hypothetical path "T" for the current tracklet is a combination of the likelihood of the individual hypotheses for the current tracklet and the transition probabilities of adjacent tracklets. The transition probability that the medical device switches state from the $j^{th}$ hypothesis at the $i^{th}$ tracklet to the $k^{th}$ hypothesis at the $(i+1)^{th}$ tracklet may be expressed as follows:

$$q_{i,j,k}=Pr(t_{i+1}=h_{i+1,k}|t_i=h_{i,j}) \quad (2)$$

which is a combination of static prior knowledge of connectivity in the computer model of the branched anatomical structure and dynamic knowledge of which lumen branching out of a node indicated by the current tracklet was entered by the medical device. The static prior knowledge of connectivity in the computer model of the branched anatomical structure may be obtained, for example, by performing a patient scan using a suitable imaging modality to capture image slices from which an accurate three-dimensional computer model of the branched anatomical structure may be generated. The dynamic knowledge of which lumen branching out of a node indicated by the current tracklet was entered by the medical device may be obtained, for example, by programming the processor with artificial reasoning which follows analytical reasoning as described herein.

The most likely match for the current sequence of tracklets is then based upon the most likely hypothetical path taken by the medical device. As an example, the solution may be the path that maximizes the combined probability expressed as follows:

$$T^*=\operatorname{argmax}_T Pr(O|T) \quad (3)$$

One technique for efficiently solving the above discrete path optimization problem is using Dynamic Programming (DP), similar to the inference algorithm in the Hidden Markov Model (HMM).

After completing processing of block 509, the method then redefines the new tracklet as the current tracklet in block 510 and loops back to block 501 to expand on and process the new current tracklet which was previously detected in block 504. The method then continues to loop through blocks 501-510 as the medical device continues to move through the branched anatomical structure.

Although the various aspects of the present invention have been described with respect to one or more embodiments, it will be understood that the invention is entitled to full protection within the full scope of the appended claims.

What is claimed is:

1. A system comprising:
memory that stores information representing a model of an anatomical structure of a human;
a medical device including a distal end that is configured to be inserted into the anatomical structure, the distal end supporting an image capturing device configured to capture sequential images as the medical device is moved through branches of the anatomical structure; and
one or more processing devices configured to access the information representing the model of the anatomical structure, the one or more processing devices further configured to:
process the captured sequential images to detect one or more blobs in individual images, the one or more blobs representing lumens within the anatomical structure;
identify, from at least one image of the captured sequential images, a first captured sequence that represents information on a first set of one or more lumens within the anatomical structure;
identify, from at least one image of the captured sequential images, a second captured sequence that represents information on a second set of one or more lumens within the anatomical structure, wherein the second captured sequence follows the first captured sequence in the captured sequential images and the second set of lumens is different from the first set of lumens;
generate a sequence of synthetic images from the information representing the model of the anatomical structure;
determine that the generated sequence of synthetic images substantially matches a current captured sequence comprising the first captured sequence and the second captured sequence, and
responsive to the determination that the generated sequence of synthetic images substantially matches the current captured sequence:
identify, from the sequence of synthetic images, a portion of the model representing a navigational path within the anatomical structure from the first set of one or more lumens to the second set of one or more lumens; and
determine a location of the distal end of the medical device within the anatomical structure based on a location represented by the navigational path within the model of the anatomical structure.

2. The system of claim 1 wherein the one or more processing devices are further configured to:
process a first image in the captured sequential images to identify one or more first blobs representing corresponding lumens in the anatomical structure;
process a second image in the captured sequential images to identify one or more second blobs representing corresponding lumens in the anatomical structure;
determine that the one or more second blobs substantially matches the one or more first blobs; and
responsive to the determination that the one or more second blobs substantially matches the one or more first blobs, label each of the first image and the second image as being a part of the first captured sequence or the second captured sequence.

3. The system of claim 1, wherein the one or more processing devices are further configured to:
process a first image in the captured sequential images to identify one or more first blobs representing corresponding lumens in the anatomical structure;
process a second image in the captured sequential images to identify one or more second blobs representing corresponding lumens in the anatomical structure;
determine that the one or more second blobs are substantially different from the one or more first blobs; and
responsive to the determination that the one or more second blobs are substantially different from the one or more first blobs, label the first image as being a part of the first captured sequence or the second captured sequence, and label the second image as being a part of a sequence that is different from that for the first image.

4. The system of claim 3, wherein the one or more processing devices are further configured to label images from two different sequences as being part of a single unified captured sequence.

5. The system of claim 4, wherein the one or more processing devices are further configured to:
determine that the generated sequence of synthetic images substantially matches the current captured sequence, which also includes the unified captured sequence.

6. The system of claim 1, wherein determining that the generated sequence of synthetic images substantially matches a current captured sequence comprises:
identifying that a plurality of candidate sequences, generated based on the model of the anatomical structure, match the current captured sequence;
generating a match score for each of the plurality of candidate sequences; and
identifying, based on the match scores, one of the plurality of candidate sequences as the generated sequence of synthetic images that substantially matches the current captured sequence.

7. The system of claim 6, wherein identifying that a plurality of candidate sequences matches the current captured sequence comprises:
identifying a set of feature attributes of one or more blobs represented in a candidate sequence;
calculating, based on the set of feature attributes, a metric indicative of a similarity between the one or more blobs from one of the plurality of candidate sequences and one or more blobs in the current captured sequence; and
identifying that the one of the plurality of candidate sequences matches the current captured sequence responsive to determining that the metric satisfies a threshold condition.

8. The system of claim 7, wherein the set of feature attributes includes one or more of: a number, shapes, sizes, locations, and orientations of the one or more blobs.

9. The system of claim 1, wherein determining that a generated sequence of synthetic images substantially matches the current captured sequence comprises:
identifying, in the current captured sequence of images, a transition point between the first captured sequence and the second captured sequence;
identifying, based on the transition point, one or more connected lumens;
identifying a plurality of candidate sequences based on locations of connected lumens in the model of the anatomical structure, the plurality of candidate sequences being generated from the model of the anatomical structure; and identifying one of the plurality of the candidate sequences as the generated sequence of synthetic images that substantially matches the current captured sequence.

10. The system of claim 9, wherein the one or more processing devices are further configured to:
   determine a transitional probability for each of the plurality of the candidate sequences, the transitional probability indicating a quality of match for a transition from one lumen to another in the model of the anatomical structure; and
   determine one of the plurality of the candidate sequences as the generated sequence of synthetic images based on the transitional probabilities calculated for the plurality of the candidate sequences.

11. The system of claim 9, wherein identifying the plurality of candidate sequences is based also on position information received from a position sensor disposed in the medical device.

12. The system of claim 9, wherein identifying the plurality of candidate sequences is based also on orientation information received from an orientation sensor disposed in the medical device, the orientation sensor configured to measure an orientation of the distal end of the medical device relative to a fixed horizontal plane.

13. The system of claim 9, wherein identifying the plurality of candidate sequences is based also on roll information from a roll sensor disposed in the medical device, the roll sensor configured to measure a roll angle of the medical device about a longitudinal axis of the medical device.

14. The system of claim 9, wherein identifying the plurality of candidate sequences is based also on insertion information received from an insertion sensor disposed in the medical device, the insertion sensor configured to measure an insertion distance of the distal end of the medical device into the anatomical structure.

15. A method for determining a position of a distal end of a medical device within an anatomical structure of a human, the distal end configured to be inserted into the anatomical structure, the method comprising:
   receiving representations of sequential images captured using an image capturing device supported by the distal end of the medical device;
   accessing, by one or more processing devices, information representing a model of the anatomical structure;
   processing, by the one or more processing devices, the captured sequential images to detect one or more blobs in individual images, the one or more blobs representing lumens within the anatomical structure;
   identifying, from at least one image of the captured sequential images, a first captured sequence that represents information on a first set of one or more lumens within the anatomical structure;
   identifying, from at least one image of the captured sequential images, a second captured sequence that represents information on a second set of one or more lumens within the anatomical structure, wherein the second captured sequence follows the first captured sequence in the captured sequential images and the second set of lumens is different from the first set of lumens;
   generating a sequence of synthetic images from the information representing the model of the anatomical structure;
   determining that the generated sequence of synthetic images substantially matches a current captured sequence comprising the first captured sequence and the second captured sequence; and
   responsive to the determination that the generated sequence of synthetic images substantially matches the current captured sequence:
      identifying, from the sequence of synthetic images, a portion of the model representing a navigational path within the anatomical structure from the first set of one or more lumens to the second set of one or more lumens; and
      determining a location of the distal end of the medical device within the anatomical structure based on a location represented by the navigational path within the model of the anatomical structure.

16. The method of claim 15, further comprising:
   processing a first image in the captured sequential images to identify one or more first blobs representing corresponding lumens in the anatomical structure;
   processing a second image in the captured sequential images to identify one or more second blobs representing corresponding lumens in the anatomical structure;
   determining that the one or more second blobs substantially matches the one or more first blobs; and
   responsive to the determination that the one or more second blobs substantially matches the one or more first blobs, label each of the first image and the second image as being a part of the first captured sequence or the second captured sequence.

17. The method of claim 15, further comprising:
   processing a first image in the captured sequential images to identify one or more first blobs representing corresponding lumens in the anatomical structure;
   processing a second image in the captured sequential images to identify one or more second blobs representing corresponding lumens in the anatomical structure;
   determining that the one or more second blobs are substantially different from the one or more first blobs; and
   responsive to the determination that the one or more second blobs are substantially different from the one or more first blobs, label the first image as being a part of the first captured sequence or the second captured sequence, and label the second image as being a part of a sequence that is different from that for the first image.

18. The method of claim 15, wherein determining that the generated sequence of synthetic images substantially matches a current captured sequence comprises:
   identifying that a plurality of candidate sequences, generated based on the model of the anatomical structure, matches the current captured sequence;
   generating a match score for each of the plurality of candidate sequences; and
   identifying, based on the match scores, one of the plurality of candidate sequences as the generated sequence of synthetic images that substantially matches the current captured sequence.

19. The method of claim 18, wherein identifying that a plurality of candidate sequences matches the current captured sequence comprises:
   identifying a set of feature attributes of one or more blobs represented in a candidate sequence;
   calculating, based on the set of feature attributes, a metric indicative of a similarity between the one or more blobs from one of the plurality of candidate sequences and one or more blobs in the current captured sequence; and
   identifying that the one of the plurality of candidate sequences matches the current captured sequence responsive to determining that the metric satisfies a threshold condition.

20. One or more machine-readable storage devices having encoded thereon instructions configured to cause one or more processing devices to perform operations comprising:

receiving representations of sequential images captured using an image capturing device supported by a distal end of a medical device configured to be inserted into an anatomical structure of a human;

accessing information representing a model of the anatomical structure;

processing the captured sequential images to detect one or more blobs in individual images, the one or more blobs representing lumens within the anatomical structure;

identifying, from at least one image of the captured sequential images, a first captured sequence that represents information on a first set of one or more lumens within the anatomical structure;

identifying, from at least one image of the captured sequential images, a second captured sequence that represents information on a second set of one or more lumens within the anatomical structure, wherein the second captured sequence follows the first captured sequence in the captured sequential images and the second set of lumens is different from the first set of lumens;

generating a sequence of synthetic images from the information representing the model of the anatomical structure;

determining that the generated sequence of synthetic images substantially matches a current captured sequence comprising the first captured sequence and the second captured sequence; and responsive to the determination that the generated sequence of synthetic images substantially matches the current captured sequence:

identifying, from the sequence of synthetic images, a portion of the model representing a navigational path within the anatomical structure from the first set of one or more lumens to the second set of one or more lumens; and determining a location of the distal end of the medical device within the anatomical structure based on a location represented by the navigational path within the model of the anatomical structure.

* * * * *